(12) United States Patent
Briggs et al.

(10) Patent No.: US 8,552,168 B2
(45) Date of Patent: Oct. 8, 2013

(54) NUCLEIC ACIDS FOR INDUCING EXPRESSION OF TRANSCRIPTS AND PROTEINS AND METHODS FOR MAKING AND USING THEM

(75) Inventors: Steven P. Briggs, Del Mar, CA (US); Kiyoshi Tachikawa, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 690 days.

(21) Appl. No.: 12/599,577

(22) PCT Filed: May 8, 2008

(86) PCT No.: PCT/US2008/063081
§ 371 (c)(1),
(2), (4) Date: Jul. 19, 2010

(87) PCT Pub. No.: WO2008/141096
PCT Pub. Date: Nov. 20, 2008

(65) Prior Publication Data
US 2010/0306880 A1    Dec. 2, 2010

Related U.S. Application Data

(60) Provisional application No. 60/917,364, filed on May 11, 2007.

(51) Int. Cl.
*C07H 21/04* (2006.01)
*C12N 15/00* (2006.01)
*C12N 15/82* (2006.01)
*C12N 15/74* (2006.01)
*C12N 1/20* (2006.01)
*C12N 1/00* (2006.01)
*C12N 1/12* (2006.01)
*C12P 21/06* (2006.01)

(52) U.S. Cl.
USPC .......... 536/23.4; 435/455; 435/468; 435/471; 435/69.1; 435/320.1; 435/252.3; 435/252.33; 435/254.1; 435/255.1; 435/257.1; 800/278

(58) Field of Classification Search
None
See application file for complete search history.

(56) References Cited

U.S. PATENT DOCUMENTS
2006/0292629 A1* 12/2006 Kuhne et al. .................. 435/7.1

OTHER PUBLICATIONS

Kuwano et al, Molec. Gen. Genet., 154, p. 279-285, 1977.*
Schnetz et al PNAS, vol. 89(4), p. 1244-1248, 1992.*
Chen et al, Nuc Acid Res, 22, p. 4953-4957, 1994.*
Ma et al, J Bacteriol, 184(20), p. 5733-5745, 2002.*
Rajarao et al (FEMS Microbiology Letters, 215, p. 267-272, 2002).*
Tan et al, Journal of Cell Biology, 135(6), p. 1789-1800, 1996.*
Hunt et al, Genes & Dev, 13, p. 437-438, 1999.*
Twyman et al, Trends in Biotechnology, 21(12), p. 570-578, 2003.*

* cited by examiner

*Primary Examiner* — Cathy Worley
*Assistant Examiner* — Stephen Uyeno
(74) *Attorney, Agent, or Firm* — Gregory P. Einhorn; Gavrilovich, Dodd & Lindsey LLP

(57) ABSTRACT

The invention provides nucleic acids and polypeptides for enhanced expression of nucleic acids and proteins. In one aspect, the sequences serve as transcription and translation enhancers or stabilizers, and can be incorporated in expression constructs at or near the translation control elements. The invention provides methods of producing mRNA (transcripts) and proteins. The invention provides methods of discovering new enhancer elements.

18 Claims, 5 Drawing Sheets

Figure 1A pSB022 (SEQ ID NO:2) M G Y K K S N N P F S D -NLS-GFP-FLAG
(c-TES) (SEQ ID NO:1) atg ggc tat aag aaa tct aac aat ccg ttt tct gat pSB023 (SEQ ID NO:4) M V Y K K R N N R F K D -NLS-GFP-FLAG
(modified c-TES) atg gtt tat aag aaa aga aac aat aga ttt aaa gat (SEQ ID NO:3)

pSB041 M -NLS-GFP-FLAG
(point mutant) atc ggc tat aag aaa tct aac aat ccg ttt tct gat g pSB042 M -NLS-GFP-FLAG
---- ---- ---- ---- ---- ---- ---- ---- ---- ---- ---- atg pSB077 (SEQ ID NO:6) M G I R N L T I R F L I -NLS-GFP-FLAG
(Frameshift atg ggc ata aga aat cta aca atc cgt ttt ctg att (SEQ ID NO:5)
mutant)

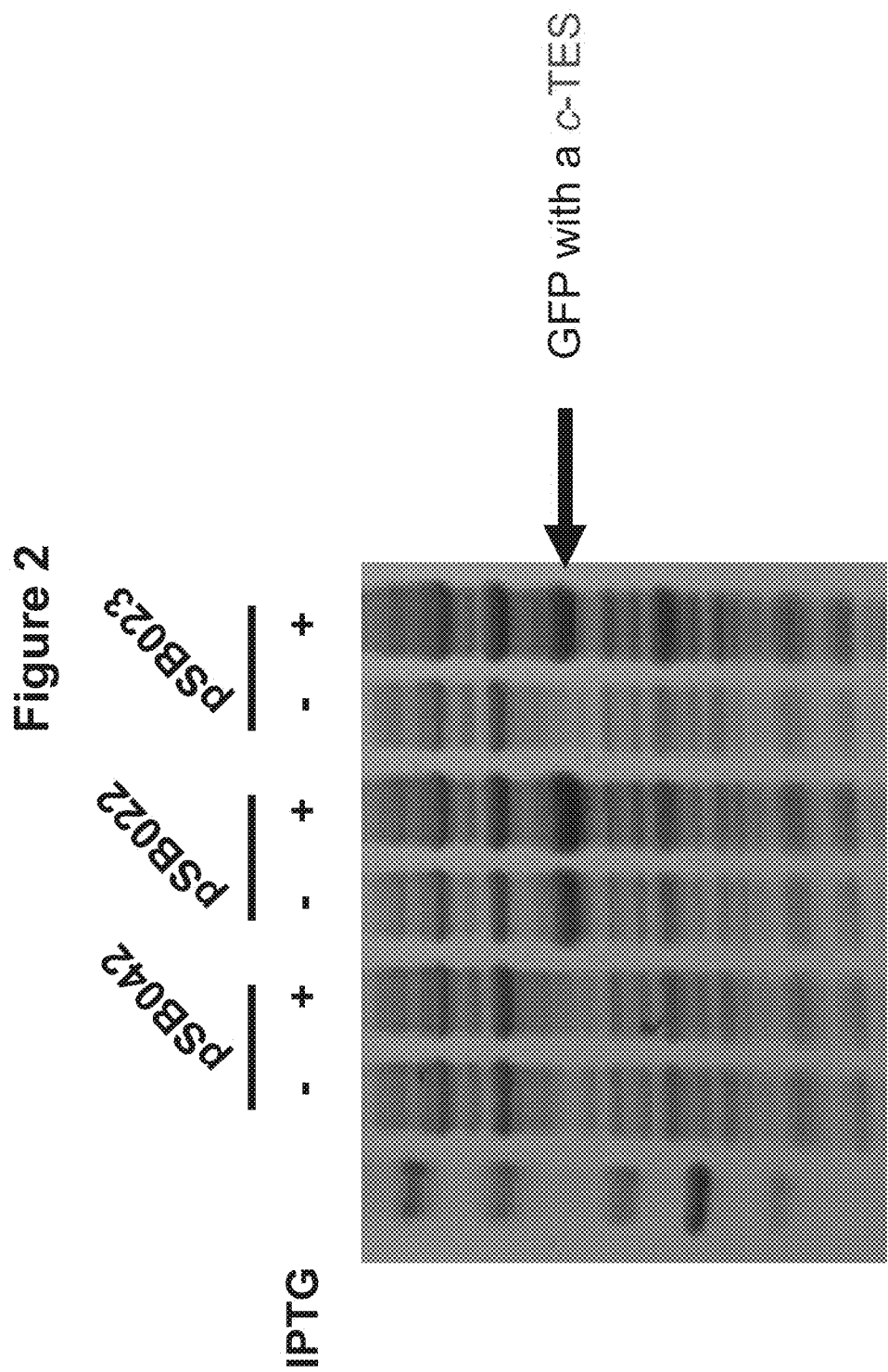

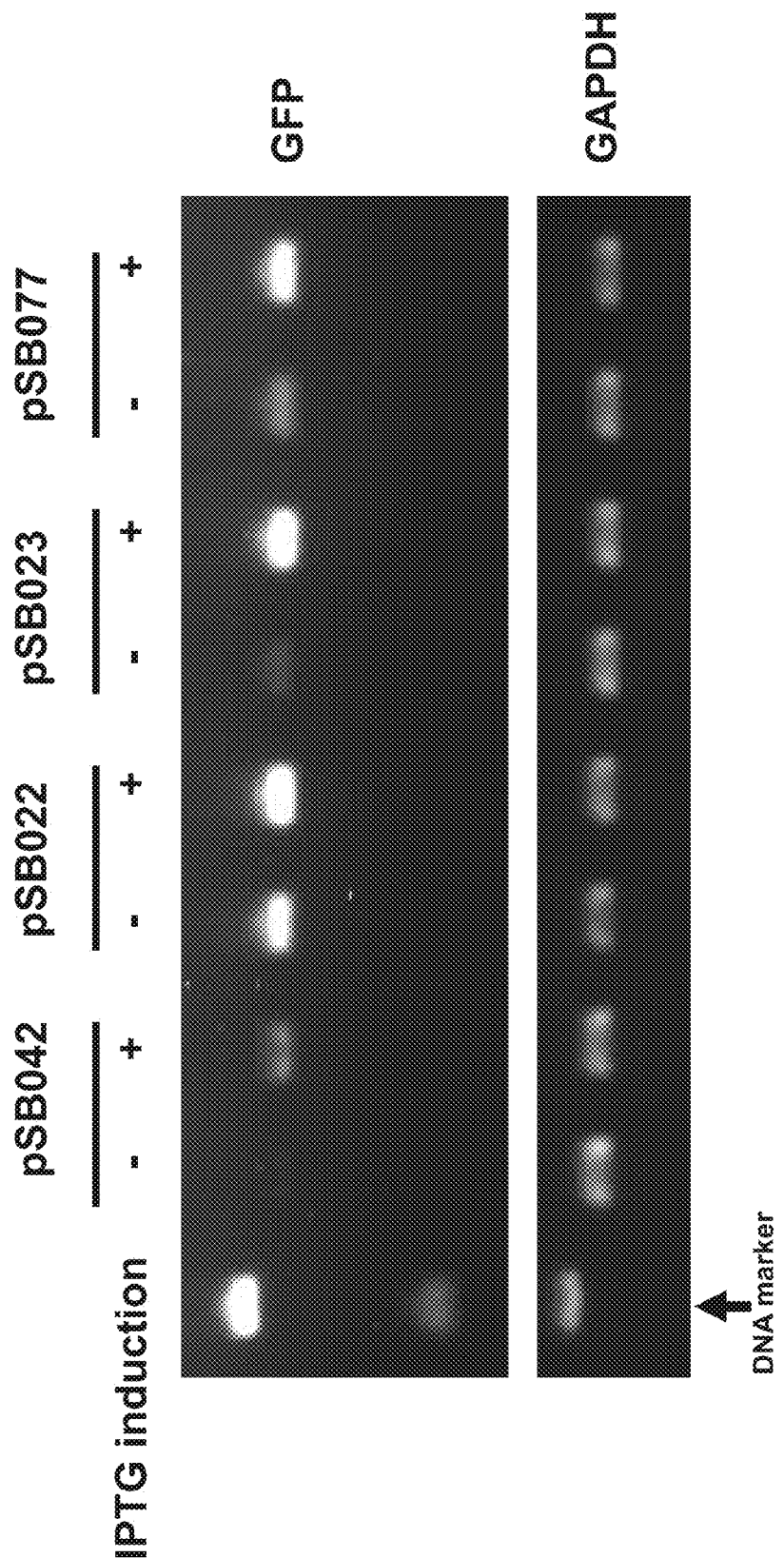

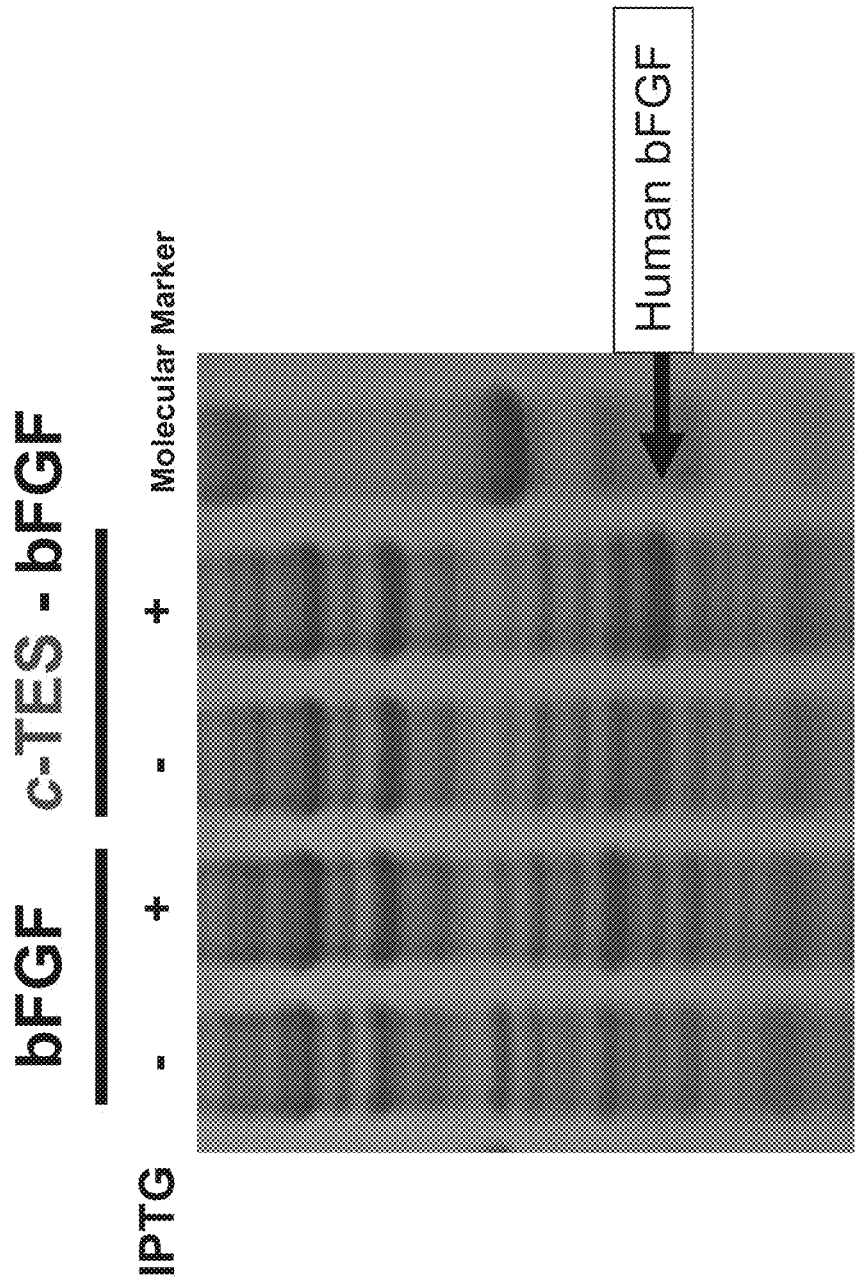

NUCLEIC ACIDS FOR INDUCING EXPRESSION OF TRANSCRIPTS AND PROTEINS AND METHODS FOR MAKING AND USING THEM

RELATED APPLICATIONS

This U.S. utility patent application is a national phase under 35 USC 371 of international patent application PCT/US2008/063081, filed May 8, 2008, which has as a priority document (claims the benefit of priority of) U.S. Provisional Application No. 60/917,364, filed May 11, 2007. The aforementioned applications are expressly-explicitly incorporated herein by reference in their entirety and for all purposes.

TECHNICAL FIELD

The present invention generally relates to the fields of molecular biology, cell expression systems and biofuels. More specifically, the invention relates to nucleotides and amino acids and compositions comprising them, where the nucleotides and amino acids are used to control expression and/or stabilization of transcripts (messages) and polypeptides, e.g., in cells; and cell expression systems and biofuel production systems comprising use of these compositions of the invention.

BACKGROUND

The expression of proteins from various organisms can be accomplished in heterologous host cells to produce active and useful products. Numerous host organisms have been developed for such expression, and each organism has its own particular requirements for successful expression of heterologous proteins. Likewise, numerous different expression vectors or constructs have been devised to allow for expression of proteins of interest in host organisms of interest.

Expression of a heterologous protein in a host cell may require that the nucleotide sequence encoding the protein be: 1) suitable for expression in the host cell (e.g., have appropriate codon usage rules applied); 2) operably linked to expression control elements that are functional in the host cell (e.g., fused to a promoter that functions in the host cell); and 3) encode a protein that is not toxic to the cell when expressed.

To express a protein that is toxic to a host cell, many solutions have been devised. One solution is to express the protein under tightly controlled conditions such that expression of the protein is totally or nearly totally repressed until an inducer of expression is provided. Some expression systems can be triggered to express large amounts of protein upon introduction of an appropriately controlled inducer. Production of such large amounts of the toxic protein can results in death of the host cell, but not until after adequate amounts of the protein of interest are produced.

Specific expression vectors for expressing toxic proteins recombinantly in host cells have been developed, including incorporation of regulatory sequences in controlling and enhancing expression of recombinant proteins.

There is a continuing need for improved sequences to enable controlled expression of recombinant or toxic proteins. In particular, elements for potent over-expression of mRNA and protein are needed to allow for higher levels of recombinant protein expression and for expression of toxic or recalcitrant proteins in host cells.

SUMMARY

The invention provides isolated, purified, synthetic or recombinant nucleic acids for increased expression or increased stabilization of an mRNA (transcript) and/or polypeptide, wherein the nucleic acid comprises, or consists of:

(a) a nucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% sequence identity, or more, or complete (100%) sequence identity, to 5'-atgggctataagaaatctaacaatccgttttctgat-3' (SEQ ID NO:1), wherein the nucleic acid acts as an enhancer of transcription when it is operatively linked to or is in close proximity to a second nucleic acid sequence, or the nucleic acid acts as to stabilize the mRNA (transcript) and/or polypeptide;

(b) the nucleic acid sequence of (a), wherein the transcription-enhanced second nucleic acid sequence comprises a protein-encoding sequence, a protein-encoding transcript or a protein-encoding gene;

(c) the nucleic acid sequence of (a) or (b), wherein the nucleic acid enhancer of transcription is operatively linked to or is in close proximity to: a Shine-Dalgarno sequence (Shine-Dalgarno box); a Kozak sequence (Kozak consensus sequence); a transcription start site; a promoter, an enhancer, a translational start site; a splice site; and/or a ribosomal binding site;

(d) the nucleic acid sequence of any of (a) to (c), wherein the close proximity is being within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more nucleic acid residues;

(e) the nucleic acid sequence of any of (a) to (d), wherein the nucleic acid sequence further comprises sequence encoding a protein localization signal;

(f) the nucleic acid sequence of (e), wherein the protein localization signal comprises a FKDE (SEQ ID NO:7) or CFFKDEL (SEQ ID NO:8) motif, or a PFS or a VLTNEN-PFSDP (SEC) ID NO:9) or YKKSNNPFSD (SEQ ID NO:10) containing motif;

(g) the nucleic acid sequence of any of (a) to (d), wherein the nucleic acid sequence further comprises a Shine-Dalgarno sequence (Shine-Dalgarno box); a Kozak sequence (Kozak consensus sequence); a transcription start site; a translational start site; a promoter; an enhancer; a splice site; and/or a ribosomal binding site;

(h) the nucleic acid sequence of any of (a) to (g), wherein the nucleic acid sequence is inserted into a vector, a cloning vehicle, an expression cassette, an expression system, an expression vector, a cloning vector or a cloning vehicle, or a viral vector, a plasmid, a phage, a phagemid, a cosmid, a fosmid, a bacteriophage or an artificial chromosome, or a bacterial artificial chromosome (BAC), a plasmid, a bacteriophage P1-derived vector (PAC), a yeast artificial chromosome (YAC), or a mammalian artificial chromosome (MAC); or (i) the nucleic acid sequence of any of (a) to (h), wherein the nucleic acid sequence is about at least 20, 21, 22, 23, 24, 25, 26, 27, 28, 29, 30, 31, 32, 33, 34, 35, 36, 37, 38, 39 or 40 or more nucleic acid residues in length.

In one embodiment, the nucleic acid comprises, or consists of, a sequence as set forth in SEQ ID NO:3 and/or SEQ ID NO:1, a so-called "TEnBox".

The invention provides vectors, cloning vehicles or expression cassettes comprising (a) a nucleic acid of the invention, and/or a nucleic acid encoding a polypeptide of the invention;

(b) the nucleic acid of (a), wherein the transcription-enhanced second nucleic acid sequence comprises a protein-encoding sequence, a protein-encoding transcript or a protein-encoding gene;

(c) the nucleic acid of (a) or (b), wherein the nucleic acid is operatively linked to or is in close proximity to: a Shine-Dalgarno sequence (Shine-Dalgarno box); a Kozak sequence (Kozak consensus sequence); a transcription start site; a translational start site; a promoter; an enhancer; a splice site; and/or a ribosomal binding site;

(d) the nucleic acid of any of (a) to (c), wherein the close proximity is being within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or more nucleic acid residues;

(e) the nucleic acid of any of (a) to (d), wherein the nucleic acid sequence further comprises sequence encoding a protein localization signal; or (f) the nucleic acid sequence of (e), wherein the protein localization signal comprises a FKDE (SEQ ID NO:7) or CFFKDEL (SEQ ID NO:8) motif, or a PFS or a VLTNEN-PFSDP (SEC) ID NO:9) or YKKSNNPFSD (SEQ ID NO:10) containing motif.

The invention provides vectors host cells comprising a nucleic acid of the invention or a vector of the invention; e.g., wherein the host cell is a bacterial cell, a mammalian cell, a fungal cell, a yeast cell, an insect cell, an algae cell or a plant cell. The host cell can be derived from a seaweed, a red seaweed, a cell from the genus *Porphyra, Gracilaria, Grateloupia, Kappaphycus* or *Ceramium*, a green seaweed, a cell from the genus *Ulva*, a brown seaweed, a kelp, a cell from the genus *Laminaria*, or a *Laminaria japonica*

The invention provides transgenic plants or seeds comprising a nucleic acid of the invention or a vector of the invention; the plant can be a seaweed, a red seaweed, from the genus *Porphyra, Gracilaria, Grateloupia, Kappaphycus* or *Ceramium*, a green seaweed, from the genus *Ulva*, a brown seaweed, a kelp, from the genus *Laminaria*, or a *Laminaria japonica*.

The invention provides isolated, purified, synthetic or recombinant polypeptides comprising, or consisting of:

(a) an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% sequence identity, or more, or complete (100%) sequence identity, to MGYKKSNNPFSD (SEQ ID NO:2), wherein nucleic acid encoding the polypeptide acts as an enhancer of transcription when it is operatively linked to or is in close proximity to a second nucleic acid sequence, or, the polypeptide acts as a protein stabilization sequence or a protein localization signal; or (b) the polypeptide of (a), wherein the polypeptide comprises a protein localization signal;

(c) the polypeptide of (a) or (b) further comprising an amino acid sequence encoding a protein localization signal; or (d) the nucleic acid sequence of (c), wherein the protein localization signal comprises a FKDE (SEQ ID NO:7) or CFFKDEL (SEQ ID NO:8) motif, or a PFS or a VLTNEN-PFSDP (SEQ ID NO:9) or YKKSNNPFSD (SEQ ID NO:10) containing motif.

The invention provides compositions comprising a nucleic acid of the invention, a vector of the invention, a host cell of the invention, a transgenic plant or seed of the invention or a polypeptide of the invention, or any combination thereof.

The invention provides immobilized polypeptides or nucleic acids: (a) wherein the polypeptide comprises a nucleic acid of the invention, a vector of the invention or a polypeptide of the invention; or, (b) the immobilized polypeptide of (a), wherein the polypeptide or nucleic acid is immobilized on a cell, a metal, a resin, a polymer, a ceramic, a glass, a microelectrode, a graphitic particle, a bead, a gel, a plate, an array or a capillary tube.

The invention provides methods of expressing an mRNA (transcript) in a cell, comprising (i) (a) providing a nucleic acid of the invention, a vector of the invention or a nucleic acid encoding a polypeptide of the invention; and, (b) expressing the nucleic acid of (a); or (ii) the method of (i), wherein the cell is a bacterial cell, a mammalian cell, a fungal cell, a yeast cell, an insect cell, an algae cell or a plant cell.

The invention provides methods for enhancing expressing an mRNA (transcript), comprising (i) (a) providing the nucleic acid of claim 1, and a second nucleic acid; (b) operatively linking or joining in close proximity the nucleic acid of claim 1 with the second nucleic acid to generate a chimeric nucleic acid; and, (c) expressing the chimeric nucleic acid of (b); or (ii) the method of (i), further comprising inserting the chimeric nucleic acid of (b) into a cell and expressing the chimeric nucleic acid in the cell;

(iii) the method of (i), comprising expressing the chimeric nucleic acid in vitro;

(iv) the method of (ii), wherein the cell is a bacterial cell, a mammalian cell, a fungal cell, a yeast cell, an insect cell, an algae cell or a plant cell, the cell can be derived from a seaweed, a red seaweed, a cell from the genus *Porphyra, Gracilaria, Grateloupia, Kappaphycus* or *Ceramium*, a green seaweed, a cell from the genus *Ulva*, a brown seaweed, a kelp, a cell from the genus *Laminaria*, or a *Laminaria japonica;*

(v) the method of any of (i) to (iv), wherein the nucleic acid of claim 1 acts as an enhancer of transcription and is operatively linked to or is in close proximity to: a Shine-Dalgarno sequence (Shine-Dalgarno box); a Kozak sequence (Kozak consensus sequence); a transcription start site; a translational start site; a promoter; an enhancer; a splice site; and/or a ribosomal binding site; or (vi) the method of (v), wherein the close proximity is being within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or more nucleic acid residues of a Shine-Dalgarno sequence (Shine-Dalgarno box); a Kozak sequence (Kozak consensus sequence); a transcription start site; a translational start site; a promoter; an enhancer; a splice site; and/or a ribosomal binding site.

In one embodiment of the method, the nucleic acid of the invention, and/or the second nucleic acid encode a protein, and the method further comprises expressing the chimeric nucleic acid to generate a recombinant polypeptide, and purifying or isolating the recombinant protein.

The invention provides methods for making a nucleic acid or amino acid sequence that can affect expression or stabilization of an mRNA (transcript) or a protein comprising (a) inserting a nucleotide sequence between a transcription start site and a translation start site, and (b) determining (measuring) the effect of the insertion on the expression of an mRNA (transcript) operatively linked to the transcription start site and/or a protein operatively linked to the translational start site;

wherein the nucleotide sequence is a sequence variation of SEQ ID NO:1;

(b) the method of (a), wherein the nucleotide sequence comprises the nucleic acid of the invention;

(c) the method of (a), wherein the sequence variation of SEQ ID NO:1 is generated by random or directed mutagenesis, or the nucleotide sequence comprises sequence derived from a genome of an organism; or (d) the method of (c), wherein the sequence derived from the genome of an organism is generated by random cloning of genomic fragments.

The invention provides methods cell expression systems for expressing a recombinant polypeptide of interest comprising (i) a host cell comprising the nucleic acid of the invention, or the vector of the invention, wherein the nucleic acid encodes a polypeptide; or (ii) the cell expression of (i), wherein the cell is a bacterial cell, a mammalian cell, a fungal cell, a yeast cell, an insect cell, an algae cell or a plant cell.

In one embodiment of the cell expression system, the recombinant polypeptide is or comprises an enzyme, for example, an enzyme to be used to make a pharmaceutical, or in biofuel production, e.g., for bioalcohol or biodiesel fuel production in a microorganism, e.g., including plants, bacteria, algae, yeast, insect cells and the like.

The invention provides nucleotides and amino acids for controlling the expression of recombinant proteins in host cells. In one embodiment, the nucleotide and amino acid sequences of the invention are relatively short, e.g., approximately 9 to 300 nucleotides in length, e.g., from 3 to 100 amino acid residues in length, for example, about 30 nucleotides and approximately 10 amino acid residues in length.

In one embodiment, the nucleotide and amino acid sequences of the invention are operatively linked to nucleic acids sequences to be expressed, e.g., as protein encoding sequences, to have an effect to increase mRNA (transcript) expression and/or protein expression. In one aspect, nucleotide and amino acid sequences of the invention are engineered to be in close proximity to a Shine-Dalgarno sequence (or Shine-Dalgarno box), and/or a Kozak sequence, or Kozak consensus sequence; e.g., close proximity being about 1, 2, 3, 4, 5, 6, 7, 8, 9, 10, 11, 12, 13, 14, 15, 16, 17, 18, 19 or 20 or more residues. For example, nucleotide and amino acid sequences of the invention are engineered to be in close proximity a ribosomal binding site, e.g., a ribosomal binding site located about 1, 2, 3, 4, 5, 6, 7, 8, 9, 10, 11, 12, 13, 14, 15, 16, 17, 18, 19 or 20 or more nucleotides residues upstream of a start codon AUG. In natural systems the Shine-Dalgarno sequence exists only in prokaryotes and it has a six-base consensus sequence AGGAGG (SEQ ID NO:11); thus, in one aspect, the invention provides nucleotide and amino acid sequences of the invention are operatively linked to prokaryotic nucleic acid sequences for expression. The eukaryotic equivalent of the Shine-Dalgarno sequence is called the Kozak sequence, or Kozak consensus sequence, for example, a eucaryotic Kozak sequence is (gcc)gccRccAUGG (SEQ ID NO:12); thus, the invention provides nucleotide and amino acid sequences of the invention are operatively linked to eukaryotic nucleic acid sequences for expression.

In one aspect, the nucleotide and amino acid sequences of the invention are used for expression of proteins in host cells and as guides for discovery of other sequences having similar effects.

In one aspect, the invention provides nucleotide sequences that can increase expression of mRNA and protein. The nucleotide sequences of the invention are not limited in size, and in alternative embodiments can comprise about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more nucleotide residues.

In one aspect, a nucleotide sequence of the invention can comprise a sequence that is translated into a protein localization signal, e.g., as described by Rajarao et al. (2002) FEMS Microbiology Letters; 215: 267-272, or a derivative of it. For example, a nucleotide sequence of the invention can comprise sequence that is translated into a protein localization signal comprising a FKDE (SEQ ID NO:7) or CFFKDEL (SEQ ID NO:8) motif, or their functional derivatives, e.g., for a delivery across the membranes of E. coli-like. A nucleotide sequence of the invention can comprise sequence that is translated into a protein localization signal comprising the S. aureus PFS containing motif, e.g., VLTNENPFSDP (SEQ ID NO:9), or the B. subtilis the PFS containing motif YKKSN-NPFSD (SEQ ID NO:10).

In another aspect, nucleotide sequences of the invention can comprise sequence that is translated into protein localization signal that penetrate into a cell, e.g., a bacterial cell, an algae or a yeast, e.g., homologs of the S. cerevisiae alpha factor, e.g., for a yeast cell specific delivery. Exemplary sequences that can be incorporated into sequence of this invention including sequences for delivery into various yeast strains, e.g., a described in Riezman et al., 1997; Cell 91, 731-738 and in Rajarao et al. (2002) FEMS supra, including sequences that are translated into motifs comprising: PFS-, YQR-, PFR-, PMF- and/or DCMD (SEQ ID NO:13) -containing motifs.

In another aspect, nucleotide sequences of the invention can comprise nuclear import sequences and motifs.

Various deletions, additions, and substitutions may be made to protein localization signals and nuclear import sequences used to practice this invention, while retaining the transcriptional and/or translational enhancing functions of the nucleic acids and polypeptides of this invention. In some aspects, alterations to the sequence improve various functions of the sequence in different host organisms and in combination with different proteins.

In another aspect, the invention provides amino acid sequences that can affect expression of proteins to which they are fused. The amino acid sequences of the invention are not limited in size, and in alternative embodiments can comprise an active region of about 10, 11, 12, 13, 14, 15, 16, 17, 18, 19, 20, 21, 22, 23, 24, 25, 26, 27, 28, 29 or 30 or more amino acid residues. For example, the invention provides isolated, purified, synthetic or recombinant polypeptides comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% sequence identity, or more, or complete (100%) sequence identity, to MGYKKSN-NPFSD (SEQ ID NO:2), and in alternative embodiments these sequences can act as protein stabilization sequences or protein localization signals.

In alternative embodiments, the amino acid sequence comprises a protein localization sequence, e.g., as disclosed by Riezman et al., 1997, supra, or Rajarao et al. (2002); or variations thereof. In one aspect, sequences to be incorporated into the compositions of this invention are altered as compared to known sequences incorporated into the compositions of this invention to provide, e.g., altered or improved expression in a selected organism.

In a further aspect, the invention provides a method of expressing mRNA molecules, proteins, or both in a cell comprising use of compositions of this invention. In general, the method comprises expressing an mRNA and/or protein from a nucleic acid molecule that comprises a nucleotide sequence of the invention. The method can, in embodiments, be a method of increasing the expression of a protein, as compared to the same protein in a similar construct, but which does not contain the nucleic acid sequence according to the invention. In an alternative embodiment, the method can be a method of purifying or isolating a recombinant protein of interest.

In one aspect, the invention provides a method of discovering new sequences that increase or otherwise enhance expression of proteins from an expression construct, such as an expression vector. In general, the method comprises inserting a nucleotide sequence of this invention between, e.g., a transcription start site and a translation start site, or any other location. In one aspect, a nucleic acid of this invention, e.g., the so-called "TEnBox", is placed upstream or downstream of a T7 promoter, an SD, or a translation initiation ATG codon, or in between SD and ATG, and the like.

In one aspect, the invention provides a method for determining the effect of the insertion on mRNA and/or protein expression comprising use of a nucleotide sequence of the invention, which can also include sequences developed by mutagenesis of a sequence of the invention. In alternative embodiments, the sequence used in this method comprises a sequence that is naturally occurring in an organism, but not naturally operably linked to the mRNA or protein-encoding sequences.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of embodiments of the invention and are not meant to limit the scope of the invention as encompassed by the claims.

FIG. 1A shows a set of selected amino acid sequences, and selected corresponding nucleic acid sequences, used in constructs of embodiments of the invention.

FIG. 2 shows a Coomassie Blue stained protein gel of protein expression results for expression of proteins in host cells harboring three plasmid constructs according to the present invention.

FIG. 3 shows Northern Blot results for expression of mRNA from cells harboring four plasmid constructs according to the present invention.

FIG. 4 shows a Coomassie Blue stained protein gel of protein expression of a recombinant protein according to the present invention.

Like reference symbols in the various drawings indicate like elements.

Figure 1B:
FIG. 1B shows results of expression experiments with the various constructs disclosed in FIG. 1A.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION OF THE INVENTION

The present invention provides nucleic acids, proteins, and compositions of matter, as well as a method to achieve significantly higher levels of transcription and protein expression from a plasmid grown in a host cell, including bacterial, such as E. coli, plant, insect, algae and yeast cells. The invention provides an enhancer of nucleic acid and/or protein expression, referred to herein variously as "c-TES", "TEnBox", or derivatives of it. The invention is predicated, at least in part, on the discovery of the RNA and protein expression enhancer function of an approximately 30 base pair DNA fragment (also referred to herein as "CSYK" (SEQ ID NO:14).

As demonstrated below, production of recombinant proteins in host cells, such as bacterial cells, such as E. coli, and plant, insect, algae and/or yeast cells, is dramatically increased when c-TES (this term encompassing all the nucleic acids of this invention) is incorporated into an expression construct, including any, vector, e.g., an expression cassette, an expression vector, a cloning vector or a cloning vehicle, or a viral vector, a plasmid, a phage, a phagemid, a cosmid, a fosmid, a bacteriophage or an artificial chromosome, or a bacterial artificial chromosome (BAC), a plasmid, a bacteriophage P1-derived vector (PAC), a yeast artificial chromosome (YAC), or a mammalian artificial chromosome (MAC).

The efficiency of the protein expression when using the c-TES sequence of the invention, which include derivatives of the c-TES sequence of the invention, such as pSB022 (see e.g., Example 1, below), is much higher than reported with the best commercial vectors; e.g., pET-21 or pTriEX-3 (Novagen, Merck KGaA, Darmstadt, Germany). Further, by incorporating the c-TES sequences of the invention into an expression system, levels of expression are better than seen with the best translation enhancing elements or downstream boxes. In one aspect, in contrast to the existing translation enhancing elements or downstream boxes that interact with their complementary sequence within 16S rRNA in the 30S ribosomal subunit to enhance translation efficiency, the c-TES and derivatives of the invention induce gene expression by increasing the transcript level.

In one embodiment of a nucleic acid of the invention, referred to as pSB023 (see e.g., Example 1, below), the nucleic acid is regulated by IPTG and is useful for, among other things, expressing proteins that are toxic to host cells (e.g., E. coli). This exemplary plasmid is not leaky, and its expression is tightly regulated by IPTG. As with using other nucleic acids of this invention, use of pSB023 demonstrated high-yield production of recombinant proteins, such as growth hormones, peptides, enzymes, industrial proteins, and therapeutic proteins in host cells can lead to obtaining high quality protein with less running cost.

There are numerous uses for the nucleic acids and proteins of the invention. They may be provided, for example by molecular biology reagent companies, to researchers who want stronger promoters/enhancers in their plasmids. Likewise, they may be provided to companies that want to use it for increasing protein expression levels for a commercial product, e.g., a biomedical product, or for producing biofuels such as bioalcohol or biodiesel (e.g., lipids). Through use of the nucleic acids and polypeptides of this invention, proteins that previously were incapable of being produced in large quantities or under highly controlled conditions can now be produced effectively. With biotechnology-derived products increasingly replacing small molecule products in the biomedical industry, the present invention finds very broad utility in both the research reagent market and in the "production of biologicals" market (e.g., therapeutics market).

It has been found that the nucleic acids of this invention (the so-called "c-TESs") can strongly increase the expression of heterologous (e.g., "foreign") nucleic acids, e.g., genes or any protein coding sequence, when they are incorporated into a vector, a cloning vehicle, an expression cassette, an expression system, an expression vector, a cloning vector or a cloning vehicle, or a viral vector, a plasmid, a phage, a phagemid, a cosmid, a fosmid, a bacteriophage or an artificial chromosome, or a bacterial artificial chromosome (BAC), a plasmid, a bacteriophage P1-derived vector (PAC), a yeast artificial chromosome (YAC), or a mammalian artificial chromosome (MAC); and in alternative embodiment the nucleic acids of this invention are incorporated in a manner that operatively links it to the heterologous (e.g., "foreign") nucleic acids, e.g., genes or any protein coding sequence. For example, in one aspect, a nucleic acid of the invention acts as an enhancer of transcription when it is operatively linked to or is in close proximity to a second nucleic acid sequence, or the nucleic acid acts as to stabilize the mRNA (transcript) and/or polypeptide.

In one aspect, such an "operative" linking (e.g., as in operatively linked to) can result in high-yield production (e.g., any yield greater than wild type) of the recombinant proteins encoded by a heterologous (e.g., "foreign") nucleic acid, e.g., genes or any protein coding sequence. Exemplary embodiments provide an mRNA and a nucleic acid of the invention acting as an enhancer of transcription (e.g., as a protein expression enhancer) that is currently combined with a promoter, e.g., a bacterial or viral promoter such as a T3 or T7 promoter, for high-level expression of proteins of interest.

In one exemplary embodiment, a version of a nucleic acid of the invention acting as an enhancer of transcription, the so-called "pSB023", is not leaky and is useful for expressing proteins that are toxic to a bacterial cell, e.g., an E. coli. This exemplary construct of the invention comprises three more basic amino acid residues (two arginines and a lysine) in its c-TES motif compare to the exemplary c-TES, the so-called pSB022. Extensive testing of the pSB023 has been performed in multiple laboratories, and each laboratory has reported high protein expression levels, which is correlated with high mRNA expression levels.

In one aspect, the invention provides nucleic acid molecules that can affect expression and/or stability of mRNA and protein molecules. The nucleotide sequences of the invention are not limited in length, but generally comprise an active region of about 30 nucleotides; or the nucleic acid sequence of the invention is about at least 20, 21, 22, 23, 24, 25, 26, 27, 28, 29, 30, 31, 32, 33, 34, 35, 36, 37, 38, 39 or 40 or more nucleic acid residues in length. In one aspect, the length is from about 24 nucleotides to about 36 nucleotides, or about 20 nucleotides to about 40 nucleotides. In one aspect, the nucleotide sequences of the invention can encode a polyamino acid sequence having at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more contiguous amino acids, e.g., at least 7, at least 8, or at least 9 contiguous amino acids. In exemplary embodiments, the nucleotide sequence can encode 10 or 11 contiguous amino acids. In some cases, the nucleotide sequence encodes a polyamino acid sequence that is linked to a protein sequence for a protein of interest.

In exemplary embodiments, nucleotide sequences of the invention comprise or consist of, or have a sequence identity based on, a yeast sequence encoding a protein localization sequence: 5'-atgggctataagaaatctaacaatccgttttctgat-3' (SEQ ID NO:1), which encodes the amino acid sequence MGYKKSNNPFSD (SEQ ID NO:2).

In alternative embodiments, a nucleotide sequence of the invention can comprise the sequence: 5'-atggtttataagaaaagaaacaatagatttaaagat-3' (SEQ ID NO:3), which encodes the amino acid sequence MVYKKRNNRFKD (SEQ ID NO:4); or 5'-atgggcataagaaatctaacaatccgttttctgatt-3' (SEQ ID NO:5), which encodes the amino acid sequence MGIRNLTIRFLI (SEQ ID NO:6).

Nucleotide sequences of the invention can be made or obtained in many ways. For example, a nucleotide sequence of the invention for enhancing mRNA expression or stabilization or for enhancing protein expression or stabilization can be designed by altering the sequence of SEQ ID NO:1 to convert it from a yeast sequence to one that has the codon preference for a host cell in which a protein is to be expressed. Thus, for example, where the nucleotide sequence is intended to enhance expression of a protein in a bacteria, e.g., an E. coli, the yeast sequence of SEQ ID NO:1 can be altered such that it continues to encode the same amino acid sequence, but does so using the codon preference of E. coli. In the same fashion, the yeast sequence can be altered such that it contains the codon preference for any other host cell, including, but not limited to, those of prokaryotes, such as gram negative bacteria (e.g., *Escherichia, Salmonella, Klebsiella* species), gram positive bacteria (e.g., *Bacillus, Clostridium* species), and archea (e.g., *Methanococcus*); and those of eukaryotes, such as yeasts and other fungi, algae, plants, and animals (e.g., primates, rodents, birds, fish, insects) in either the nuclear or organellar compartments (e.g., the plastidic or mitochondrial organelles). In alternative embodiments, sequences of the invention are designed to achieve a specific goal, such as tight control of expression, high level of expression, specific expression in only certain cells/strains, etc.

In alternative embodiments, in addition to or alternatively, changes to the sequence of SEQ ID NO:1 can be made to delete or add one or more nucleotides. In alternative embodiments, such a deletion or addition does not alter the coding frame of the nucleotide molecule. In alternative embodiments, if additions or deletions are made, they comprise an addition or deletion of a multiple of three (e.g., 3, 6, 9, 12 etc.) nucleotides. The addition or deletion of nucleotides need not concern contiguous nucleotides, but rather can include additions, deletions, or both of any nucleotide bases within the entire sequence.

In alternative embodiments, nucleic acids of the invention can comprise part of a larger nucleic acid. For example, they can be present as part of any number of vectors, e.g., cloning or expression vectors, expression cassettes, plasmids, recombinant viruses, etc. for expression of one or more proteins in a host cell. Such vectors, expression cassettes, plasmids, recombinant viruses, etc. include, but are not limited to, plasmids, phages, phagemids, cosmids, recombinant (e.g., artificial) chromosomes, and the like. Other non-limiting types of vectors for which the nucleic acids of the invention may be part include extrachromosomal elements for maintenance of genetic constructs (e.g., maintenance plasmids) and vectors for insertion of exogenous nucleic acid material into a host chromosome or genome. In alternative embodiments, the type of nucleic acid that the nucleic acid of the invention can be a part is unlimited. Those of skill in the art are fully aware of such vectors, and each vector need not be described in detail here. Further, techniques for movement of nucleic acid element in and out of vectors are well known to those of skill in the art, and thus need not be detailed here.

The present invention provides the nucleic acids of the invention as purified or isolated, or recombinant, or synthetic molecules. In alternative embodiments, they thus are provided outside of the context in which they are normally found in nature. In alternative embodiments, the nucleic acids of the invention can also be provided as a part of compositions; these compositions may be any compositions that comprise the nucleic acids of the invention (alone or as part of a fusion construct) and one other substance. In alternative embodiments, other substance(s) may be any substance(s) that are compatible (i.e., do not destroy or render inoperable) the nucleic acids of the invention. In alternative embodiments, at least one of the substances is a solvent for the nucleic acid (e.g., water, an organic solvent), or a substance that assists in solubilization of the nucleic acid (e.g., a salt). In some embodiments, one or more reagents, enzymes, etc. that are useful in cloning/subcloning, expression, or detection of nucleic acids or proteins are included in the composition.

The invention also provides purified or isolated, or recombinant, or synthetic polypeptide (e.g., polyamino acid) molecules comprising amino acid sequences that can affect expression and cellular location of proteins to which they are fused. In some embodiments, the amino acid sequences are encoded by the nucleic acids of the invention. The amino acid sequences are not limited in length; however, they can alternatively comprise about 6 to 14 contiguous amino acids. In some embodiments, they comprise an active region of about 10 (e.g., 8, 9, 10, 11, 12) contiguous residues. In some embodiments, the amino acid sequence comprises SEQ ID NO:2 or sequence having a specific sequence identity to SEQ ID NO:2; for example, it may show about 80%, 81%, 82%, 83%, 84%, 85%, 86%, 87%, 88%, 89%, 90%, 91%, 92%, 93%, 94%, 95%, 96%, 97%, 98%, 99% sequence identity, or more, or complete (100%) sequence identity to SEQ ID NO:2.

Sequences showing less than 100% identity to SEQ ID NO:2 may be derived from SEQ ID NO:2 by addition, deletion, or alteration of one or more residues of SEQ ID NO:2. For example, one or more amino acids may be deleted from the sequence of SEQ ID NO:2. Likewise, one or more amino acid residues may be added to the sequence of SEQ ID NO:2. In addition or alternatively to addition and/or deletion of residues, residues of SEQ ID NO:2 may be changed to another amino acid. The alterations can be conservative (e.g., a hydrophobic residue for another hydrophobic residue) or non-conservative (e.g., a positively charged residue for a negatively charged residue, or a charged residue for an uncharged residue).

In alternative embodiments, polypeptides (e.g., polyamino acid molecules) of the invention can be made in any suitable manner. In alternative embodiments, they are encoded by a nucleic acid sequence having the appropriate sequence. In alternative embodiments, they are made by any other suitable method, such as de novo chemical synthesis.

In alternative embodiments, an amino acid sequence of the invention is fused to a sequence of another polypeptide (e.g., polyamino acid molecule) (e.g., a protein of interest) by any suitable method. In alternative embodiments, the coding sequence for the amino acid sequence of the invention is fused in frame to the coding sequence for the other polypeptide (e.g., polyamino acid molecule), and expression of the fusion nucleic acid construct results in production of a fusion protein comprising the amino acid sequence of the invention.

The amino acid sequences of the invention can be fused to heterologous amino acid sequences to provide a fusion protein. The fusion protein can comprise any other protein of interest fused to the amino acid sequence of the invention. Fusion of the two can be performed for any purpose, e.g., can be performed to increase production or stability of the protein, or for localization of the protein in a pre-defined cell or cellular organelle. To achieve these various goals, the sequence of the polyamino acid of the invention can be altered (e.g., having a sequence identity based on SEQ ID NO:2) to improve expression in the host cell of interest, or to enhance the localization function of the polyamino acid within the context of the fusion protein and target cell.

In alternative embodiments, compositions comprising polypeptides (e.g., polyamino acids) of the invention are provided. In alternative embodiments, compositions of the invention comprise polypeptides (e.g., polyamino acids), independently or as part of a larger fusion protein, and one or more other substances. In alternative embodiments, the other substance is not limited in its identity or amount, but in one aspect is not deleterious to the stability and function of the polypeptides (e.g., polyamino acids) of the invention. In alternative embodiments, the other substance(s) are water or another suitable solvent, or a substance that participates in maintaining the polyamino acid in a stable and/or active state. In alternative embodiments, the other substance(s) are substances that are present in enzymatic reactions or in assays for detection of protein presence or activity, or in protein purification schemes. In some embodiments, nucleic acids and/or polypeptides (e.g., polyamino acids) of the invention are present in a cell or cell lysate or any in vitro system, e.g., an in vitro translation system.

In alternative embodiments, the invention provides a method of expressing mRNA molecules, proteins, or both in a cell. A method of the invention can comprise expressing an mRNA and/or protein from a nucleic acid molecule that comprises a nucleic acid and/or polypeptide of the invention. The method can comprise creating a nucleic acid molecule comprising a nucleotide sequence of the invention, and inserting or exposing the nucleic acid molecule to conditions that permit expression of one or more mRNA molecules from the nucleic acid molecule.

In alternative embodiments, methods may further comprise permitting expression of one or more polyamino acids (i.e., peptides, polypeptides, proteins) from the mRNA. In one aspect, the method comprises: introducing one or more nucleic acid molecules of the invention (which include the vectors, expression systems etc of the invention) into a host cell; and expressing at least one nucleic acid and/or protein of interest from this nucleic acid molecule(s). This exemplary method allows for high-level expression and controlled expression of mRNA and proteins.

The method may further comprise providing adequate time and conditions to allow the cell to amplify the nucleic acid molecules prior to expression of the mRNA and protein. In alternative embodiments, the method comprises repressing or otherwise limiting expression of the mRNA and protein until a signal is provided for expression. For example, expression may be induced by addition of a chemical inducer, by temperature change, by removal of an inhibitor, or any other means of inducing or de-repressing expression. Those of skill in the art are well aware of systems for controlled expression of mRNA and proteins, and any such system or combination of systems may be provided. Indeed, the present invention provides a new system for affecting expression, which can be used alone or in combination with other systems.

In alternative embodiments, the method comprises, by use of a nucleic acid of the invention, increasing the expression of a protein as compared to the same protein in a similar construct which does not contain the nucleic acid of the invention. In these embodiments, the method can comprise: introducing one or more nucleic acids of the invention into a host cell; providing adequate time and conditions for high-level expression of the nucleic acid(s), and in particular mRNA and protein corresponding to the nucleic acid(s). The method can comprise comparing the expression levels of the mRNA, the protein, or both to the expression of mRNA and/or protein from host cells comprising a similar nucleic acid construct, but lacking the nucleic acid sequence of the invention.

All assays, methods, etc. according to the invention can be practiced with one or more control reactions for each step. As is well understood in the art, control reactions can be easily be designed and implemented to ensure that assay steps are performed successfully and to the level expected (or to provide a baseline or benchmark for a reaction). Design of adequate control reactions, including positive controls or negative controls, is well within the skill of the skilled artisan, and thus need not be detailed herein.

In alternative embodiments, the method may also be a method of purifying or isolating a recombinant protein of interest. In this regard, the method may comprise some or all of the steps described herein, and can further include the step of purification or isolation of the expressed polypeptide (polyamino acid molecule). Purification and isolation may follow any suitable series of steps. For example, where crude purification is required, the method may comprise lysing the host cell and separating insoluble materials from soluble materials. The purification scheme may further comprise purifying the protein of interest by way of one or more protein precipitation steps (e.g., salt precipitation), one or more column chromatography steps (e.g., hydrophobic interaction, size exclusion, anion or cation exchange, and affinity binding). While any level of purification or isolation is encompassed by the methods of this invention, e.g., separation of the protein of interest from any other substances, in alternative embodiments the protein is purified to more than 50% purity, more than 75% purity, more than 90% purity, more than 95% purity, about or more than 98% purity, about or more than 99% purity, or about or 100% purity. Purity can be assayed by any number of techniques, including Coomassie blue staining, silver staining, Western blot, and amino acid sequencing.

In alternative embodiments, the invention provides a method of localizing a protein of interest to a cell or cellular organelle. The amino acid sequence of SEQ ID NO:2 is adequate for localization of proteins fused to it into microbial cells; in one embodiment it is known as an endocytosis signal for the Kex2p protein of yeast, which participates in localization of proteins in yeast and bacterial cells. In alternative embodiments, nucleic acids and/or polypeptides of the invention are used to localize proteins to any cell or cell compartment, e.g., to any internal membrane-delineated compartment within a cell, e.g., an organelle, nucleus, chloroplast, mitochondria, golgi apparatus and the like. The nucleic acids and/or polypeptides of the invention thus may be used to localize proteins to the nucleus of eukaryotic cells, including those of plants, algae, yeast, insects, fungi and animals. Likewise, the nucleic acids and/or polypeptides of the invention may be used to localize proteins to chloroplast cells of plants and algae, and mitochondria of eukaryotic cells, e.g., fungal, yeast or animal cells. In alternative embodiments, the nucleic acids and/or polypeptides of the invention can be used to traffic proteins both into and out of cells, such as mammalian and other higher-level eukaryotic cells.

In alternative embodiments, the method of localizing proteins comprises: providing a nucleic acid and/or polypeptide of the invention; providing a cell of interest; providing conditions under which the protein of interest (e.g., encoded by a nucleic acid comprising a sequence of this invention, or recombinantly fused to a polypeptide of this invention) can be localized into the cell, out of the cell, or to or from a membrane-delineated compartment (e.g., nucleus, chloroplast, or any vesicle) of the cell, wherein the protein is localized, at least in part, as a result of the presence of the nucleic acid and/or polypeptide of the invention.

In one aspect, the method comprises contacting the protein with the cell and allowing a sufficient amount of time for the protein to enter the cell and localize to the cell interior or a specific compartment within the cell interior. In some embodiments, the method comprises: fusing a nucleic acid sequence of the invention to a nucleotide sequence encoding a desired protein, or fusing an amino acid sequence of the invention to a desired protein; expressing the desired protein; and exposing the desired protein to a cellular membrane for a sufficient amount of time and under appropriate conditions to allow the desired protein to traverse one or more membranes, resulting in localization of the desired protein in a cell or cellular organelle. Expression of the protein may be within the cell of interest or may be in another cell. The cell may be any type of cell (e.g., prokaryotic or eukaryotic; algae, fungal, yeast, insect, plant or animal) and localization may be to any cell or cell organelle, vesicle, membrane or compartment.

In one aspect, the invention provides a method of discovering new sequences that increase or otherwise enhance expression of proteins from an expression construct, such as an expression vector. In some embodiments, the method comprises inserting a nucleotide sequence of this invention between a transcription start site and a translation start site, and determining the effect of the insertion on mRNA and/or protein expression. In one aspect, the effect is determined by detecting one or more characteristics of the protein. In one aspect, the protein of the construct has a detectable characteristic, such as, but not limited to, enzymatic activity, and antigenicity, intrinsic color expression.

In alternative embodiments, the nucleotide sequence being assayed for expression enhancement comprises a sequence of the invention. Because the sequences of the invention have certain levels of expression enhancement when fused to other nucleotide or amino acid sequences, those of skill in the art can easily devise derivatives having similar activities, and can customize the sequences for expression in various organisms. In one aspect, sequences of the invention are mutated in a random or pre-defined manner, then assayed for activity in one or more organisms or cells, or in vitro, or in the context of one or more proteins. Thus, in alternative embodiments, new sequences which enhance expression are generated.

In alternative embodiments, the sequence to be determined is a sequence that naturally occurs in an organism, but is not naturally operably linked to the mRNA or protein-encoding sequences of the construct to be used for assay of activity. That is, constructs of the invention may be designed that include transcription control elements linked to translation control elements. In alternative embodiments, these two elements are interrupted by insertion of random sequences from an organism of interest, and a library of constructs can be created. In alternative embodiments, this library is assayed for changes in expression patterns, as compared to the construct that does not include the insert, and nucleic acid molecules having interesting properties isolated and studied.

In alternative embodiments, expression cassettes of the invention comprise a nucleotide sequence of the invention, which are capable of affecting expression of a structural gene (i.e., a protein coding sequence) in a host compatible with such sequences. In alternative embodiments, expression cassettes of the invention comprise nucleic acids of the invention operatively linked to or is in close proximity to: a Shine-Dalgarno sequence (Shine-Dalgarno box); a Kozak sequence (Kozak consensus sequence); a transcription start site; a translational start site; a promoter; an enhancer; a splice site; and/or a ribosomal binding site, which in turn are operatively linked to a polypeptide coding sequence; and, optionally, with other sequences, e.g., transcription termination signals. Additional factors necessary or helpful in effecting expression may also be used, e.g., enhancers. "Operably linked" as used herein can refer to linkage of a nucleic acid of the invention to a transcriptional activity, e.g., a promoter or an enhancer, which can be upstream from a DNA sequence such that the promoter mediates transcription of a nucleic acid sequence such as a protein coding sequence. Expression cassettes of the invention include plasmids, expression vectors, recombinant viruses, any form of recombinant "naked DNA"

vector, and the like. A vector of the invention can comprise a nucleic acid which can infect, transfect, transiently or permanently transduce a cell. A vector of the invention can comprise a naked nucleic acid, or a nucleic acid complexed with protein or lipid. A vector of the invention can comprise viral or bacterial nucleic acids and/or proteins, and/or membranes (e.g., a cell membrane, a viral lipid envelope, etc.). A vector of the invention can comprise replicons (e.g., RNA replicons, bacteriophages) to which fragments of DNA may be attached and become replicated. A vector of the invention can comprise RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting a vector, expression cassette, plasmid, etc, of the invention this includes both extra-chromosomal circular and linear DNA and DNA, e.g., that have or have not been incorporated into a host chromosome(s). Where a vector is being maintained by a host cell, the vector may either be stably replicated by the cells during mitosis as an autonomous structure, or is incorporated within the host's genome.

Nucleic acids and nucleic acid sequences of the invention include oligonucleotides, nucleotides, polynucleotides, or any fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., double stranded iRNAs, e.g., iRNPs). Nucleic acids and nucleic acid sequences of the invention encompass nucleic acids, i.e., oligonucleotides, containing known analogues of natural nucleotides. Nucleic acids and nucleic acid sequences of the invention encompass nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

Polypeptides and proteins of the invention include amino acids joined to each other by peptide bonds or modified peptide bonds, i.e., peptide isosteres, and may contain modified amino acids other than the 20 gene-encoded amino acids. Polypeptides and proteins of the invention also include peptides and polypeptide fragments, motifs and the like. Polypeptides and proteins of the invention also include glycosylated polypeptides.

The peptides and polypeptides of the invention also include all "mimetic" and "peptidomimetic" forms. The "mimetics" and "peptidomimetics" of the invention also include a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a transcriptional and/or translational enhancing activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-di-isopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-0), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L- naphylalanine; D- or L- phenylglycine; D- or L-2 thieneylalanine; D- or L-1, -2, 3-, or 4- pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl) carbodiimide or 1-ethyl-3(4-azonia-4, 4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, in one aspect under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4- hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

Nucleic acids of the invention can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with a primer sequence.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

The nucleic acids used to practice this invention, whether RNA, cDNA, genomic DNA, vectors, viruses or hybrids thereof, may be isolated from a variety of sources, genetically engineered, amplified, and/or expressed/ generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Alternatively, nucleic acids can be obtained from commercial sources.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., *Molecular Cloning: A Laboratory Manual* (2nd ed.), Vols. 1-3, Cold Spring Harbor Laboratory, (1989); *Current Protocols in Molecular Biology*, Ausubel, ed. John Wiley & Sons, Inc., New York (1997); *Laboratory Techniques in Biochemistry and Molecular Biology: Hybridization with Nucleic Acid Probes*, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In practicing the invention, nucleic acids of the invention or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., *PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) Proc. Natl. Acad. Sci. USA 86:1173); and, self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; and Sooknanan (1995) *Biotechnology* 13:563-564.

In various aspects, sequence comparison programs identified herein are used in this aspect used to practice the invention, i.e., to determine if a nucleic acid or polypeptide sequence is within the scope of the invention. However, protein and/or nucleic acid sequence identities (homologies) may be evaluated using any sequence comparison algorithm or program known in the art. Such algorithms and programs include, but are by no means limited to, TBLASTN, BLASTP, FASTA, TFASTA and CLUSTALW (see, e.g., Pearson and Lipman, Proc. Natl. Acad. Sci. USA 85(8):2444-2448, 1988; Altschul et al., J. Mol. Biol. 215(3):403-410, 1990; Thompson Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

In one aspect, homology or identity is measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. In one aspect, the terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. In one aspect, for sequence comparison, one sequence acts as a reference sequence, to which test sequences are compared. When using a sequence comparison algorithm, test and reference sequences are entered into a computer, subsequence coordinates are designated, if necessary and sequence algorithm program parameters are designated. Default program parameters can be used, or alternative parameters can be designated. The sequence comparison algorithm then calculates the percent sequence identities for the test sequences relative to the reference sequence, based on the program parameters.

One example of a useful algorithm to determine if a sequence is within the scope of this invention is BLAST and BLAST 2.0 algorithms, which are described in Altschul et al., Nuc. Acids Res. 25:3389-3402, 1977 and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3 and expectations (E) of 10 and the BLOSUM62 scoring matrix (see Henikoff & Henikoff, Proc. Natl. Acad. Sci. USA 89:10915, 1989) alignments (B) of 50, expectation (E) of 10, M=5, N=−4 and a comparison of both strands.

In one aspect, protein and nucleic acid sequence homologies are evaluated using the Basic Local Alignment Search Tool ("BLAST"). In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

Methods for transforming cells are well known in the art, e.g., methods for transforming algae can be used as described by U.S. Pat. No. 5,661,017.

The invention will be further explained by the following Examples, which are intended to be purely exemplary of the invention, and should not be considered as limiting the invention in any way.

EXAMPLES

Example 1

Identification and Characterization of an Expression-Enhancing Function of a Nucleic Acid of the Invention The invention provides isolated, purified, synthetic or recombinant nucleic acids for increased expression or increased stabilization of an mRNA (transcript) and/or polypeptide, wherein the nucleic acids act as an enhancer of transcription when operatively linked to or in close proximity to a second nucleic acid sequence, or the nucleic acids act as to stabilize the mRNA (transcript) and/or polypeptide. This example demonstrate the activity of exemplary nucleic acids of this invention.

As can be seen in FIGS. 1A and 1B, various enhancer sequences were designed and tested for their ability to affect the level of expression of the green fluorescent protein (GFP) within the context of a fusion protein with a nuclear localization signal (NLS) and a purification tag (FLAG) under the transcriptional control of IPTG. Within the series of constructs is: the original yeast sequence (pSB022); a modified sequence that was optimized for expression in *E. coli* and for tightly controlled expression by induction with IPTG (pSB023); a point mutant that resulted in loss of expression of all of the original residues, but retained an N-terminal methionine (pSB041); a construct that contained no nucleotide region encoding residues of the original yeast sequence except the N-terminal methionine (pSB042); and a frameshift mutation that resulted in a full-length, but altered amino acid sequence (pSB077).

FIG. 1B shows that the two constructs either lacking substantially all of the nucleotides of the enhancer (pSB042) or containing essentially all of the nucleotides, but coding for only a methionine, expressed no GFP protein in the absence of induction by IPTG, and expressed little GFP protein upon induction by IPTG. In contrast, the wild-type sequence (pSB022) showed some basal expression and high level of expression upon induction by IPTG. The leakiness of pSB022 was overcome by engineering the sequence to reduce expression in the absence of IPTG (pSB023). Interestingly, the sequence of the enhancer region appears to be somewhat involved in expression, as shown by the results for construct pSB077, which includes a frame-shift mutation, and shows low, but detectable expression in the absence of IPTG, and good expression upon induction by IPTG.

The results of FIGS. 1A and 1B indicate that both sequence presence and identity are involved in the transcription enhancement of nucleic acids of the invention. However, it is not possible, based on this data, to assign a role to either. It is, however, clear that the enhancer sequences of the invention affect transcription and/or translation of mRNA and proteins operably linked to them. While not being limited to any particular mechanism of action, it is believed that the sequences of the invention act, at least in part, in stabilization of mRNA molecules. Such stabilization allows for increased translation of protein from the mRNA, resulting in increased production of proteins of interest.

Example 2

Effect of Nucleic Acids of this Invention on Protein Production in *E. Coli*

To further characterize the effect of expression enhancer sequences of the invention on protein production, various exemplary plasmid constructs of the invention (including the so-called exemplary pSB042, pSB022, and pSB023 of the invention) were introduced into *E. coli*, and GFP fusion protein was expressed from them under the control of IPTG. The results of the experiment are shown in FIG. 2. As can be seen in the Figure, the construct lacking substantially all of the nucleotides found in an enhancer of the invention (pSB042) showed no detectable expression of the GFP protein. The "leaky" construct (pSB022) containing the original yeast sequence showed expression of GFP protein both in the absence and presence of IPTG, with IPTG induction showing a small but detectable increase in expression. In contrast, plasmid pSB023, which comprises a sequences that was optimized for tightly controlled expression by IPTG in *E. coli* showed no detectable expression in the absence of IPTG, but significant expression upon induction by IPTG.

The results shown in FIG. 2 show that constructs according to the invention can be used to direct enhanced and controlled production of fusion proteins in cells. The results also show that the nucleic acids of the invention can be customized to provide advantageous properties for expression of proteins under control of selected control elements in selected host cells.

Example 3

Effect of Nucleic Acids of this Invention on mRNA Expression

The experiments reported above show that various features of the enhancer elements of the invention are advantageous for high-level expression of fusion proteins, and for controlled expression in host cells. The results, however, do not shed light on the effect of the sequences on transcription as compared to translation. Accordingly, experiments were conducted to determine the effect of the constructs on mRNA levels in host cells. In short, *E. coli* cells were transformed with plasmids pSB042, pSB022, pSB023, and pSB077 (see above), and expression of GFP fusion protein assayed under non-induced conditions and under conditions where transcription was induced with IPTG. mRNA production was assayed by Northern blotting using a GFP-specific probe.

As can be seen in FIG. 3, mRNA expression in the null mutant pSB042 is undetectable in the absence of IPTG, and barely detectable upon induction with IPTG. Expression of the GFP fusion mRNA from the pSB022 (wild-type) plasmid can be seen to be high without induction by IPTG, and still higher upon induction. In contrast, expression of the mRNA from the optimized pSB023 plasmid in cells not exposed to IPTG is very low, whereas it is very high upon induction with IPTG. Finally, expression of mRNA from pSB077 (frameshift mutant) is low, but detectable, in the absence of induction with IPTG, and very high upon induction with IPTG. As can be seen, all of the expression levels were normalized to the housekeeping mRNA for GAPDH.

The results shown in FIG. 3 indicate that mRNA levels correlate well with the protein levels determined through the experiments described above and results shown in FIGS. 1 and 2. Thus, it appears that the effect of the expression enhancers of the invention exert their influence, at least in part, at the transcription level. While not being limited to any specific mechanism of action, the effect appears to be mediated through either transcription activation or mRNA stabilization.

Example 4

Expression of a Fusion Protein of this Invention in *E. coli*

The invention provides fusion proteins encoded by, e.g., nucleic acids of this invention, or comprising polypeptides of this invention. The experiments and results described above relate to a fusion protein comprising expression enhancers of the invention and a protein that is intrinsically detectable by colorimetric assays. To further substantiate the effects of an enhancer sequence according to the invention, the sequence of SEQ ID NO:3, encoding SEQ ID NO:4, was fused in-frame to the sequence encoding the human basic fibroblast growth factor (bFGF), and the construct expressed in *E. coli*. More specifically:

Cloning

A total of $5 \times 10^5$ HEK293 cells per well were plated onto a 24-well tissue culture-treated plate and incubated at 37° C. for 36 h in 300 µl of DMEM medium supplemented with 0.1 mM NEAAs and 10% FBS. Subsequently, 30 µl of 1 µM DRP solution in OPTI-MEM I™ (Invitrogen, Carlsbad, Calif.)

reduced serum medium was added to each well and incubated at 37° C. for 5 h. The total RNA was isolated using TRIZOL™ (Invitrogen, Carlsbad, Calif.) from human embryonic kidney cell line, HEK293 according to the accompanied protocol.

The cDNA was prepared from 1 µg of the total RNA using p(N)$_6$ primer and SUPERSCRIPT II™ RNaseH⁻ Reverse Transcriptase (Invitrogen, Carlsbad, Calif.) according to the accompanying protocol. Subsequently, the cDNA was amplified via PCR, at 94° C. for 2 min, (94° C. for 30 sec, 65° C. for 30 sec, and 72° C. for 1 min)×30 cycles, 72° C. for 10 min.

The PCR products digested with Nco I and Xho I were ligated with pET21d (+) (Novagen) digested with the same enzymes. After 1 h ligation, the DNA was transformed into TOP10 chemical competent cells (Invitrogen), culture on a LB agar plate including 100 µg/ml of ampicillin and then purified the plasmid from positive clones. The sequence for the insert was verified by DNA sequencing.

Protein Expression

*E. coli* BL21(DE3) (Invitrogen) bearing the human bFGF-coding plasmid was cultured overnight with shaking (250 rpm) at 37° C. in LB medium containing 2% glucose, 100 µg/ml ampicillin, 30 µg/ml chloramphenicol. Inoculate 300 µl of the culture into a new tube containing 6 ml of the same medium as above without glucose. When O.D. reached between 0.5 and 0.65, the protein production was induced by adding 20 µl of 100 mM IPTG and incubated for further 3 hours. The cells were collected by centrifugation at 15,000×g for 1.5 min and then analyzed by a SDS-PAGE.

Expression of bFGF in *E. coli*, either with or without the TEnBox element present, is shown in FIG. 4. As can be seen from the figure, little or no bFGF can be detected from constructs lacking the TEnBox element (lanes 1 and 2), whereas strong expression can be seen from constructs comprising the TEnBox upon induction of expression by IPTG (lanes 4 and 5). These results indicate that the expression enhancers of the invention can be used to express different proteins in host cells.

It will be apparent to those skilled in the art that various modifications and variations can be made in the practice of the invention without departing from the scope or spirit of the invention. Other embodiments of the invention will be apparent to those skilled in the art from consideration of the specification and practice of the invention. It is intended that the specification and examples be considered as exemplary only.

A number of aspects of the invention have been described. Nevertheless, it will be understood that various modifications may be made without departing from the spirit and scope of the invention. Accordingly, other aspects are within the scope of the following claims.

What is claimed is:

1. An isolated, purified, synthetic or recombinant nucleic acid, wherein the nucleic acid comprises SEQ ID NO: 3, wherein the nucleic acid is operatively linked to a second nucleic acid, and the nucleic acid acts to enhance expression of a polypeptide encoded by the second nucleic acid.

2. A vector, cloning vehicle, or expression cassette comprising:
   (a) the nucleic acid of claim 1;
   (b) the nucleic acid of (a), wherein the transcription-enhanced second nucleic acid sequence comprises a protein-encoding sequence, a protein-encoding transcript, or a protein-encoding gene;
   (c) the nucleic acid of (a) or (b), wherein the nucleic acid sequence is operatively linked to or is in close proximity to a Shine-Dalgarno sequence;
   (d) the nucleic acid of (c), wherein the close proximity of the Shine-Dalgarno sequence is within about 5 to 13 nucleic acid residues;
   (e) the nucleic acid of any of (a) to (d), wherein the nucleic acid sequence further comprises a sequence encoding a protein localization signal;
   (f) the nucleic acid of (e), wherein the protein localization signal comprises FKDE (SEQ ID NO: 7);
   (g) the nucleic acid of an of (a) to (f), wherein the nucleic acid is operatively linked to or is in close proximity to a Kozak consensus sequence;
   (h) the nucleic acid of any of (a) to (g), wherein the nucleic acid is operatively linked to or is in close proximity to a transcription start site;
   (i) the nucleic acid of any of (a) to (h), wherein the nucleic acid is operatively linked to or is in close proximity to a translation start site;
   (j) the nucleic acid of any of (a) to (i), wherein the nucleic acid is operatively linked to or is in close proximity to a promoter;
   (k) the nucleic acid of any of (a) to (j), wherein the nucleic acid is operatively linked to or is in close proximity to an enhancer;
   (l) the nucleic acid of any of (a) to (k), wherein the nucleic acid is operatively linked to or is in close proximity to a splice site;
   (m) the nucleic acid of any of (a) to (l), wherein the nucleic acid is operatively linked to or is in close proximity to a ribosomal binding site;
   (n) the nucleic acid of (e), wherein the protein localization signal comprises a CFFKDEL (SEQ ID NO: 8) motif;
   (o) the nucleic acid of (e), wherein the protein localization signal comprises a PFS or a VLTNENPFSDP (SEQ ID NO: 9) motif; or
   (p) the nucleic acid of (e), wherein the protein localization signal comprises a YKKSNNPFSD (SEQ ID NO: 10) motif.

3. The vector of claim 2, wherein the vector, cloning vehicle, expression cassette is an expression system, an expression vector, a cloning vector, cloning vehicle, a viral vector, a plasmid, a phage, a phagemid, a cosmid, a fosmid, a bacteriophage, an artificial chromosome, a bacterial artificial chromosome (BAC), a bacteriophage P1-derived vector (PAC), a yeast artificial chromosome (YAC), or a mammalian artificial chromosome (MAC).

4. A host cell comprising the nucleic acid of claim 1.

5. The host cell of claim 4, wherein the host cell is a bacterial cell, a mammalian cell, a fungal cell, a yeast cell, an insect cell, an algal cell, a plant cell, a *Porphyra* cell, a *Gracilaria* cell, a *Grateloupia* cell, a *Kappaphycus* cell, a *Ceramium* cell, an *Ulva* cell, a *Laminaria* cell, a seaweed cell, a red seaweed cell, a brown seaweed cell, a green seaweed cell, or a kelp cell.

6. A composition comprising the nucleic acid of claim 1.

7. An immobilized nucleic acid, wherein the nucleic acid comprises the nucleic acid of claim 1, wherein the nucleic acid is immobilized on a cell, a metal, a resin, a polymer, a ceramic, a glass, a microelectrode, a graphitic particle, a bead, a gel, a plate, an array, or a capillary tube.

8. A method of expressing an mRNA transcript in a cell, comprising:
   (i) (a) providing the nucleic acid of claim 1; and, (b) expressing the nucleic acid of (a); or
   (ii) the method of (i), wherein the cell is a bacterial cell, a mammalian cell, a fungal cell, a yeast cell, an insect cell, an algal cell, or a plant cell.

9. A cell expression system for expressing a recombinant polypeptide of interest comprising:
   (i) a host cell comprising the nucleic acid of claim 1, wherein the nucleic acid encodes a polypeptide; or
   (ii) the cell expression of (i), wherein the cell is a bacterial cell, a mammalian cell, a fungal cell, a yeast cell, an insect cell, an algal cell, or a plant cell.

10. The cell expression system of claim 9, wherein the recombinant polypeptide comprises an enzyme.

11. The isolated, purified, synthetic, or recombinant nucleic acid of claim 1, wherein the second nucleic acid sequence comprises a protein-encoding sequence, a protein encoding transcript, or a protein-encoding gene.

12. The isolated purified, synthetic, or recombinant nucleic acid of claim 1, wherein the nucleic acid is operatively linked to or is in close proximity to:
   (a) a Shine-Dalgarno sequence;
   (b) a Kozak consensus sequence;
   (c) a transcription start site;
   (d) a translation start site;
   (e) a promoter;
   (f) an enhancer;
   (g) a splice site;
   (h) a ribosomal binding site; or
   (i) any combination or all of (a) to (h).

13. The isolated, purified, synthetic, or recombinant nucleic acid of claim 12, wherein the close proximity of the Shine-Dalgarno sequence is within about 5 to 13 nucleic acid residues.

14. The isolated, purified, synthetic or recombinant nucleic acid of claim 1, wherein the nucleic acid sequence further comprises a sequence encoding a protein localization signal.

15. The isolated, purified, synthetic, or recombinant nucleic acid of claim 14, wherein the protein localization signal comprises:
   (a) a FKDE (SEQ ID NO: 7) motif;
   (b) a CFFKDEL (SEQ ID NO: 8) motif;
   (c) a PFS or a VLTNENPFSDP (SEQ ID NO: 9) motif; or
   (d) a YKKSNNPFSD (SEQ ID NO: 10) motifs.

16. The isolated, purified, synthetic, or recombinant nucleic acid of claim 1, wherein the nucleic acid sequence further comprises:
   (a) a Shind-Dalgarno sequence;
   (b) a Kozak consensus sequence;
   (c) a transcription start site;
   (d) a translational start site;
   (e) a promoter
   (f) an enhancer;
   (g) a splice site;
   (h) a ribosomal binding site; or
   (i) any combination of all of (a) to (h).

17. The isolated, purified, synthetic, or recombinant nucleic acid of claim 1, wherein the nucleic acid sequence is inserted into a vector, a cloning vehicle, an expression cassette, an expression system, an expression vector, a cloning vector, a cloning vehicle, a viral vector, a plasmid, a phage, a phagemid, a cosmid, a fosmid, a bacteriophage, an artificial chromosome, a bacterial artificial chromosome (BAC), a bacteriophage P1-derived vector (PAC), a yeast artificial chromosome (YAC), or a mammalian artificial chromosome (MAC).

18. The host cell of claim 5, wherein the bacterial cell is an *E. coli* cell.

* * * * *

```
                        SEQUENCE LISTING

<160> NUMBER OF SEQ ID NOS: 15

<210> SEQ ID NO 1
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 1
atgggctata agaaatctaa caatccgttt tctgat                              36

<210> SEQ ID NO 2
<211> LENGTH: 12
<212> TYPE: PRT
<213> ORGANISM: artificial sequence
<220> FEATURE:
<223> OTHER INFORMATION: synthetic peptide

<400> SEQUENCE: 2

Met Gly Tyr Lys Lys Ser Asn Asn Pro Phe Ser Asp
1               5                   10

<210> SEQ ID NO 3
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 3
atggtttata agaaaagaaa caatagattt aaagat                              36

<210> SEQ ID NO 4
<211> LENGTH: 12
<212> TYPE: PRT
<213> ORGANISM: artificial sequence
<220> FEATURE:
<223> OTHER INFORMATION: synthetic peptide
```

<400> SEQUENCE: 4

Met Val Tyr Lys Lys Arg Asn Asn Arg Phe Lys Asp
1               5                   10

<210> SEQ ID NO 5
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 5
atgggcataa gaaatctaac aatccgtttt ctgatt                              36

<210> SEQ ID NO 6
<211> LENGTH: 12
<212> TYPE: PRT
<213> ORGANISM: artificial sequence
<220> FEATURE:
<223> OTHER INFORMATION: synthetic peptide

<400> SEQUENCE: 6

Met Gly Ile Arg Asn Leu Thr Ile Arg Phe Leu Ile
1               5                   10

<210> SEQ ID NO 7
<211> LENGTH: 4
<212> TYPE: PRT
<213> ORGANISM: artificial sequence
<220> FEATURE:
<223> OTHER INFORMATION: synthetic peptide

<400> SEQUENCE: 7

Phe Lys Asp Glu
1

<210> SEQ ID NO 8
<211> LENGTH: 7
<212> TYPE: PRT
<213> ORGANISM: artificial sequence
<220> FEATURE:
<223> OTHER INFORMATION: synthetic peptide

<400> SEQUENCE: 8

Cys Phe Phe Lys Asp Glu Leu
1               5

<210> SEQ ID NO 9
<211> LENGTH: 11
<212> TYPE: PRT
<213> ORGANISM: artificial sequence
<220> FEATURE:
<223> OTHER INFORMATION: synthetic peptide

<400> SEQUENCE: 9

Val Leu Thr Asn Glu Asn Pro Phe Ser Asp Pro
1               5                   10

<210> SEQ ID NO 10
<211> LENGTH: 10
<212> TYPE: PRT
<213> ORGANISM: artificial sequence
<220> FEATURE:
<223> OTHER INFORMATION: synthetic peptide

<400> SEQUENCE: 10

Tyr Lys Lys Ser Asn Asn Pro Phe Ser Asp
1               5                   10

```
<210> SEQ ID NO 11
<211> LENGTH: 10
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (7)..(10)
<223> OTHER INFORMATION: wherein n is any nucleotide

<400> SEQUENCE: 11 aggaggnnnn                                                          10

<210> SEQ ID NO 12
<211> LENGTH: 13
<212> TYPE: RNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (7)..(7)
<223> OTHER INFORMATION: n is a, c, g, or u

<400> SEQUENCE: 12
gccgccncca ugg                                                      13

<210> SEQ ID NO 13
<211> LENGTH: 4
<212> TYPE: PRT
<213> ORGANISM: artificial sequence
<220> FEATURE:
<223> OTHER INFORMATION: synthetic polypeptide

<400> SEQUENCE: 13
```

Asp Cys Met Asp
1

```
<210> SEQ ID NO 14
<211> LENGTH: 4
<212> TYPE: PRT
<213> ORGANISM: artificial sequence
<220> FEATURE:
<223> OTHER INFORMATION: synthetic polypeptide

<400> SEQUENCE: 14
```

Cys Ser Tyr Lys
1

```
<210> SEQ ID NO 15
<211> LENGTH: 37
<212> TYPE: DNA
<213> ORGANISM: artificial sequence
<220> FEATURE:
<223> OTHER INFORMATION: synthetic polynucleotide

<400> SEQUENCE: 15
atcggctata agaaatctaa caatccgttt tctgatg                            37
```